(12) United States Patent
Richelsoph (10) Patent No.: US 7,744,636 B2
(45) Date of Patent: Jun. 29, 2010

(54) LOCKING MECHANISM

(75) Inventor: Marc E. Richelsoph, Memphis, TN (US)

(73) Assignee: Aesculap II, Inc., Center Valley, PA (US)

( * ) Notice: Subject to any disclaimer, the term of this patent is extended or adjusted under 35 U.S.C. 154(b) by 1205 days.

(21) Appl. No.: 11/015,214

(22) Filed: Dec. 16, 2004

(65) Prior Publication Data

US 2006/0149233 A1    Jul. 6, 2006

(51) Int. Cl.
*A61B 17/70* (2006.01)
(52) U.S. Cl. .......................... 606/272; 606/278; 74/470
(58) Field of Classification Search ................ 606/272, 606/278, 308, 266, 267, 279; 285/18, 308, 285/340; 74/470; 403/24, 334, 331
See application file for complete search history.

(56) References Cited

U.S. PATENT DOCUMENTS

| 2,982,573 | A | * | 5/1961 | McKee, Jr. ................ | 411/542 |
| 3,016,941 | A | * | 1/1962 | Coldren ..................... | 411/134 |
| 4,946,458 | A | | 8/1990 | Harms et al. | |
| 4,950,269 | A | * | 8/1990 | Gaines, Jr. ................. | 606/261 |
| 5,096,235 | A | * | 3/1992 | Oetiker ..................... | 285/308 |
| 5,207,678 | A | | 5/1993 | Harms et al. | |
| 5,360,431 | A | * | 11/1994 | Puno et al. ................. | 606/308 |
| 5,466,237 | A | | 11/1995 | Byrd, III et al. | |
| 5,549,608 | A | | 8/1996 | Errico et al. | |
| 5,554,157 | A | | 9/1996 | Errico et al. | |
| 5,586,984 | A | | 12/1996 | Errico et al. | |
| 5,615,965 | A | * | 4/1997 | Saurat et al. ................. | 403/24 |
| 5,683,392 | A | | 11/1997 | Richelsoph et al. | |
| 5,695,226 | A | * | 12/1997 | Gouda ........................ | 285/340 |
| 5,733,285 | A | | 3/1998 | Errico et al. | |
| 5,797,911 | A | | 8/1998 | Sherman et al. | |
| 5,891,145 | A | | 4/1999 | Morrison et al. | |
| 5,910,142 | A | | 6/1999 | Tatar | |
| 5,964,760 | A | | 10/1999 | Richelsoph | |
| 6,010,503 | A | | 1/2000 | Richelsoph et al. | |
| 6,053,917 | A | | 4/2000 | Sherman et al. | |
| 6,280,442 | B1 | | 8/2001 | Barker et al. | |
| 6,355,040 | B1 | | 3/2002 | Richelsoph et al. | |
| 6,565,566 | B1 | * | 5/2003 | Wagner et al. ............. | 606/267 |
| 6,592,585 | B2 | * | 7/2003 | Lee et al. .................... | 606/252 |
| 7,141,051 | B2 | * | 11/2006 | Janowski et al. ............ | 606/272 |
| 7,303,563 | B2 | * | 12/2007 | Poyner et al. ............... | 606/279 |

* cited by examiner

*Primary Examiner*—Pedro Philogene
(74) *Attorney, Agent, or Firm*—RatnerPrestia (57) ABSTRACT

A locking mechanism including a non-threaded, self-adjusting locking device for locking a rod in place within a screw and rod assembly. A non-threaded, self-adjusting locking device for locking a rod in place within a screw and rod assembly. A spring for locking a rod in a screw and rod fixation assembly. A assembly including an implant body including a rod seat for seating a rod therein, a biasing device seat for seating a biasing device therein, and a biasing device seated in the biasing device seat for biasing a rod against a rod seat. A method of biasing a rod against a rod seat in a screw and rod fixation assembly.

18 Claims, 6 Drawing Sheets

LOCKING MECHANISM

BACKGROUND OF THE INVENTION

1. Field of the Invention

The present invention relates to a locking mechanism. More specifically, the present invention relates to a locking mechanism for use in a screw and rod fixation assembly.

2. Description of Related Art

Stabilization of the spine for various conditions, including degenerative disc disease, scoliosis, spondylolithises, and spinal stenosis often requires attaching implants to the spine and then securing the implants to spinal rods. Such spinal fixation devices can immobilize the vertebrae and can alter the alignment of the spine over a large number of vertebrae by means of connecting at least one elongate rod to the sequence of selected vertebrae. Such rods can span a large number of vertebrae, such as three or four. However, the spine anatomy rarely allows for three or more implants to be directly in line. In order to allow for this irregularity, the rod must be contoured to the coronal plane. With anatomical curvature in the saggital plane found in the lumbar spine, the rod has to be contoured in both planes, requiring considerable effort and surgical time.

For example, the U.S. Pat. Nos. 5,554,157, 5,549,608, and 5,586,984, all to Errico et al., disclose polyaxial locking screws and coupling element devices for use with rod fixation apparatus. The '157 patent discloses a coupling element including an interior axial passage having an interior surface which is inwardly curvate at the lower portion thereof such that it comprises a socket for polyaxially retaining a spherical head of a screw. The coupling element further includes a pair of vertically oriented opposing channels extending down from the top of the coupling element which define therebetween a rod receiving seat. The channel further provides the walls of the upper portion to a pair of upwardly extending members, each including an exterior threading disposed on the upper most portion thereof for receiving a locking nut. During the implantation of the assembly, the locking nut seats against the top of the rod which in turn seats on top of the screw head. The nut causes the rod to be locked between the nut and screw and the screw to be locked in the socket.

The '608 patent discloses a modification wherein a locking ring is disposed about the exterior of the lower portion of the coupling element and provides an inward force on an outwardly tapered portion upon downward translation thereof, causing the interior chamber to crush lock a screw head therein to eliminate the polyaxial nature of the screw element coupling.

The '984 patent discloses a polyaxial orthopedic device including a coupling element having a tapered lower portion including a slotted interior chamber in which a curvate head of a screw is initially polyaxially disposed. The coupling element includes a recess for receiving a rod of the implant apparatus. A locking ring is disposed about the lower portion of the coupling element and provides an inward force on the outwardly tapered portion upon downward translation thereof. The vertical slots are caused to close and crush, thereby locking the screw head within the inter chamber thereof.

With regard to a posterial spinal fixation system, the size of the implant is an important issue. Bulky components can cause soft tissue irritation, as well as comprise the facet joints at the end of a fusion. Minimizing the size of the implants used is critical in spinal surgery with regard to the issue of bulky components. Soft tissue irritation resulting from extensions of implants is a common occurrence. Many times it is caused by the implant being too high relative to its environment. For example, implants can be too high to sufficiently be covered with muscle tissue. Hence, a reduction in the overall height of an implant is a critical advantage for the patient.

Most spine implants utilize a rod connection mechanism that requires a nut, connector, or other component to secure the implant to the rod, such as in those prior art patents discussed above. This connection means has at least some portion that sits above the rod to which the implants are connected. This increases the overall height of the implant assembly in the body.

Several attempts have been made in the prior art to address this concern of the overall height of the implant assembly. Modulok™ (manufactured by Zimmer and Wright Medical, Arlington, Tenn.), Versalok™ (manufactured by Wright Medical, Arlington, Tenn.), and Paragon™ (manufactured by DANEK, Memphis, Tenn.) are all products in the marketplace utilizing a taper connection mechanism to minimize the amount of material situated above the rod in the spinal assembly. However, these types of designs have various inherent difficulties. The Modulok™ system requires a tapered sleeve to be snapped in place over the rod prior to locking the rod to the implant. The Paragon™ system requires use of two tapered sleeves. The Versalok™ system, specifically designed for lower back fixation, requires that the rod be snapped into a channel and an outer sleeve be brought up to compress the rod interface.

All of the above-mentioned systems have drawbacks, including the bulky instrumentation needed to engage the tapers which somehow must be brought into the surgical environment, thereby causing various difficulties in surgical use. For example, a surgeon usually determines the contour of a rod by contouring the rod and placing it into the saddle or seat of the implants. Then the surgeon examines the contour, removes the rod, and re-contours the rod as required.

Others have approached the solution to this problem with various poly-axial screw designs. For example, in U.S. Pat. No. 5,466,237 to Byrd et al., a bone screw is described that includes a spherical projection on the top of the bone screw. An externally threaded receiver member supports the bone screw and a spinal rod on top of the spherical projection. An outer nut is tightened onto the receiver member to press the spinal rod against the spherical projection to accommodate various angular orientations of the bone screw relative to the rod. While this particular approach utilizes a minimum of components, the security of the fixation of the bone screw to the rod is lacking. In other words, the engagement or fixation between the small spherical projection on the bone screw and the spinal rod is readily disrupted when the instrumentation is subjected to the high loads of the spine, particularly in the lumbar region.

In another approach disclosed in U.S. Pat. No. 4,946,458 to Harms et al., a spherical headed bone screw is supported within separate halves of a receiver member. The bottoms of the halves are held together by a retaining ring. The top of the receiver halves are compressed about the bone screw by nuts threaded onto a threaded spinal rod. In another approach taken by Harms et al., in U.S. Pat. No. 5,207,678, a receiver member is flexibly connected about a partially spherical head of a bone screw. Conical nuts on opposite sides of the receiver member are threaded onto a threaded rod passing through the receiver. As the conical nuts are threaded toward each other, the receiver member flexibly compresses around the head of the bone screw to clamp the bone screw in its variable angular position. One detriment of the systems in the two Harms et al. patents is that the spinal rod must be threaded in order to accept the compression nuts. It is known that threading rods can tend to weaken the rods in the face of severe spinal loads. Moreover, the design of the bone screws in the '458 and '678 patents require a multiplicity of parts and are fairly complicated to achieve complete fixation of the bone screw.

A further approach illustrated in U.S. Pat. No. 5,797,911 to Sherman et al. is to provide a U-shaped holder through the top of which a bone fastener topped with a crown member is loaded. The holder accommodates a rod in a channel above the crown member and a compression member above the rod. The compression member presses on the rod and crown member to lock the fastener against the holder in any of a number of angles in three dimensions with respect to the rod. This approach is somewhat bulky in order to accommodate the other structural components.

Yet a further approach is disclosed in U.S. Pat. No. 5,733,285 to Errico et al., in which a holder is provided with a tapered and colletted portion at the bottom into which a bone fastener head is inserted. A sleeve is provided that slides down around the colletted portion to crush lock the colletted portion around the head of the bone fastener. This apparatus is believed to be relatively bulky and difficult to manipulate given the external sliding locking mechanism. It is further dependent on the fit of the external sleeve and the relative strength of the collet and its bending and crushing portions for secure locking of the bone fastener head.

Another important aspect for improving a polyaxial screw is having a screw head securing means that provides a strong lock while minimizing size. All known polyaxial screws in prior art require substantial size due to the locking mechanism.

For example, U.S. Pat. No. 6,280,442, to Barker et al. discloses a complex locking means having a screw head with complex head geometry, a crown member, and an outer rigid body. Locking occurs by compressing the crown member against the complex head, which compresses the head against the rigid seat. This crushes the machined ridges on the head and secures the screw.

Another example, and one common in many polyaxial screw patents, is the use of some sort of collet that has a spherical seat with a flexible portion that is designed to deflect around the screw. By compressing the flexible portion against a rigid outer wall, the collet is compressed against the head to cause locking. Such configurations are disclosed in U.S. Pat. No. 6,053,917 to Sherman et al., U.S. Pat. No. 6,010,503, to Richelsoph, and U.S. Pat. No. 5,964,760, to Richelsoph. Tartar in U.S. Pat. No. 5,910,142 discloses a spherical collet that is compressed between the screw head and the rod. U.S. Pat. No. 5,891,145 discloses a very complex double wedge locking means. The more complex the locking means the larger the components need to be and the more expensive to manufacture.

In addition, the majority of the locking mechanisms use a set screw, nut, or other threaded locking means. Threaded devices tend to be subject to cross-threading. Therefore, considerable effort must be placed into instrument design and surgeon technique to prevent this from happening. In addition, proper locking can only achieved by exerting a controlled locking force, such as a torque wrench, or a set screw designed to fracture the head portion at the proper load. Furthermore, the exertion of torque on the set screw exerts a force on the implant and bone. This detrimental load on the spine must be countered by another instrument referred to as a counter-torque instrument. This makes the surgical procedure more difficult, as room must he provided for the counter-torque instrument.

There have been other solutions. U.S. Pat. No. 5,683,392, to Richelsoph et al., discloses a non-threaded locking means whereby an outside collar is drawn upwards over an inner collet to lock the screw and rod simultaneously. This mechanism requires considerable force to engage the collar and is bulky due to the wall thickness needed in the collar to maintain compressive strength. U.S. Pat. Nos. 6,010,503 and 6,355,040, to Richelsoph show a collet that is inserted within the body portion of at implant, such that the walls of the collet deflect and bend to engage the rod and lock the assembly. While this creates a low profile, the mechanism is complex and requires significant energy to lock the system together.

The energy required to lock the system further complicates the instrumentation. Instruments become larger and more complex whenever this is an increase in required locking force. This is partly due to the energy loss in locking due to elastic and plastic deformation of the implant and elastic energy losses due to flexing of the instruments.

It would therefore be useful to develop a locking means that locks securely without exerting any torsional load on the spine, requires no torque wrench or breaking set screws, self adjusts to exert proper locking force, is uneffected by in vivo conditions (for example, blood and debris in threads), eliminates threads and the risk of cross-threading, as an efficient use of energy to allow maximum use of the locking energy without frictional or mechanical losses, can stay within known acceptable tolerances for locked components, and is small, compact, and simple.

SUMMARY OF THE INVENTION

According to the present invention, there is provided a locking mechanism including a non-threaded, self-adjusting locking device for locking a rod in place within a screw and rod assembly. A non-threaded, self-adjusting locking device for locking a rod in place within a screw and rod assembly. A spring for locking a rod in a screw and rod fixation assembly. A assembly including an implant body including a rod seat for seating a rod therein, a biasing device seat for seating a biasing device therein, and a biasing device seated in the biasing device seat for biasing a rod against a rod seat. A method of biasing a rod against a rod seat in a screw and rod fixation assembly.

DESCRIPTION OF THE DRAWINGS

Other advantages of the present invention are readily appreciated as the same becomes better understood by reference to the following detailed description, when considered in connection with the accompanying drawings wherein.

DETAILED DESCRIPTION OF THE INVENTION

Generally, the present invention provides a locking mechanism shown at 10 in the Figures. The locking mechanism 10 of the present invention is a non-threaded, self-adjusting spring locking mechanism 10.

The term "self-adjusting" as used herein is intended to include any locking mechanism 10 that includes parts therein that are capable of automatically adjusting when stress is placed on the part. Absent such stress, the part, and thus the locking mechanism 10, returns to a neutral condition.

By using a self-adjusting system, considerable complexity of a locking system can be removed from the implant and instruments. Normally, an instrument must provide for seating of the locking means as well as controlling the load at which it seats. With the implant controlling this function, the instrumentation is simplified and only serves one function, to position the locking means at the right location. The self-adjusting system also in capable of maintaining the tolerances known to those of skill in the art.

The term "implant" as used herein is intended to include any spinal implant that includes a screw and rod fixation assembly. Such assemblies are well known to those of skill in the art and can be formed using materials known to those of skill in the art.

The term "spring" as used herein is intended to define the ability of the locking mechanism 10 to flex or adjust upon the application of stress. By using a spring system, the force exerted by the locking means on the components being locked can be controlled and directed efficiently. The thickness of the spring alters the spring rate.

The spring 12 can be formed from a high strength hard material to maximize the spring rate while minimizing thickness. In addition, shape memory polymers can be used. Some of these materials are, Ti-6Al-4V heat treated to increase tensile and yield strength, Ti—Mo, Ni—Ti, better known as Nitinol, stainless steels such as 22-13-5, and other similar materials. Manufacturing can be done by machining or by forming or pressing the material into the proper shape.

Figure 1:
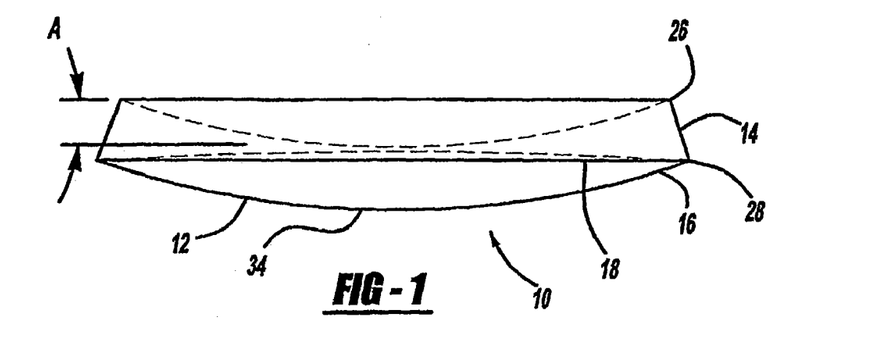
FIG. 1 is a side view of the locking mechanism of the present invention.
Figure 2:
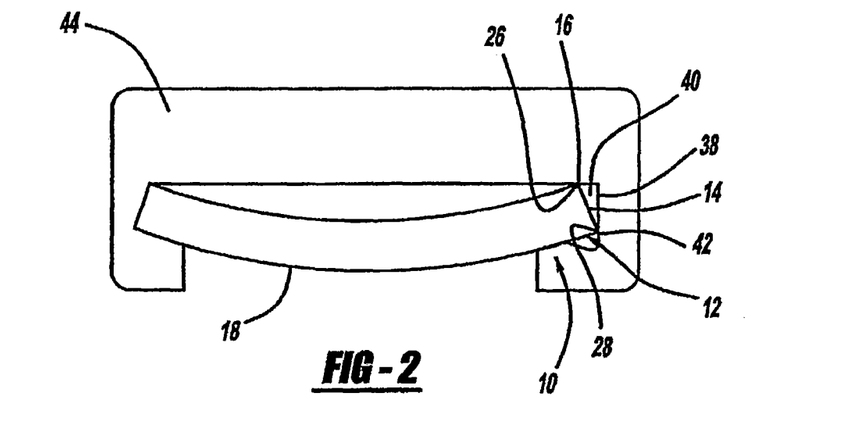
FIG. 2 is a side view of the locking mechanism of the present invention for use within a locking cap.
Figure 3:
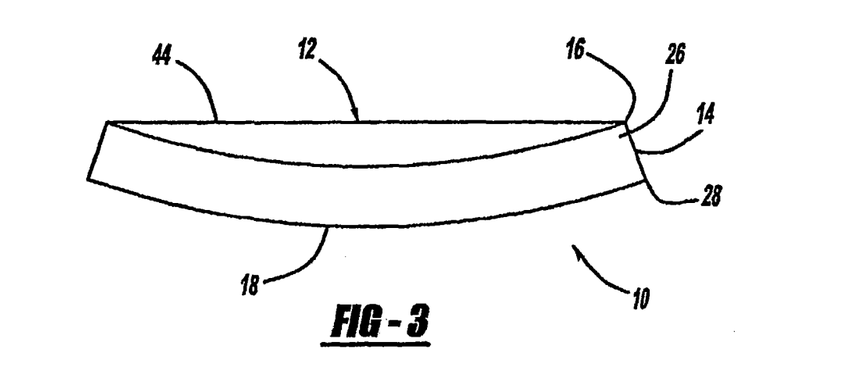
FIG. 3 is a side view of a locking mechanism of the present invention with an angled lip.
Figure 4:
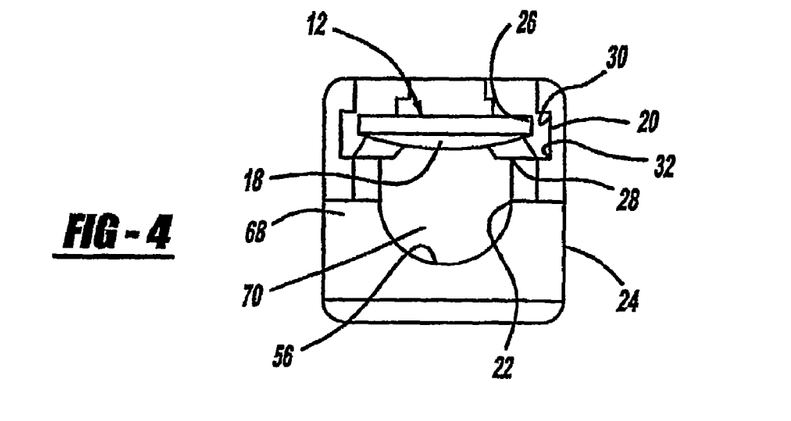
FIG. 4 is a side view of the locking mechanism of the present invention within an implant body.

The locking mechanism 10 of the present invention includes a self-adjusting spring 12 as shown in FIGS. 1 through 3. The spring 12 includes a lip 14 on the radially peripheral edge 16 of the spring 12 and a central portion 18. The lip 14 engages a groove 20 machined into an interior surface 22 of an implant body 24 as shown in FIG. 4. The lip 14 includes a top portion 26 and bottom portion 28 that respectively engage an upper edge 30 and lower edge 32 of the groove 20.

In one embodiment, the spring 12 used is in the form of a Belleville washer 12'. This type of spring 12' is a flexible disc having a wall thickness that directly affects the spring rate.

$$F_{max} = \frac{4E \cdot t^3 \cdot s_m}{(1 - \mu^2) \cdot \alpha \cdot D^2} \quad [N, lb]$$

Where:
E=Spring modulus of elasticity [MPa, psi]
t=Spring material thickness [mm, in]
$s_m$=limit spring deflection [mm, in]
μ=Poisson's ratio
α=calculation coefficient
D=outside spring diameter [mm, in]

The thicker the disc 12', the more force it takes to deflect the disc. Therefore, the amount of force exerted can be directly controlled and adjusted by altering the thickness of the disc 12'.

FIG. 1 shows a spring 12' having a curvature and wall thickness, along with a deflection range 34. The deflection range 34 is amount of motion possible before the inside radius/central portion 18 becomes flat. As force is applied against the spring 12', the spring deflects as long as the washer is appropriately flexible. As mentioned above, the thicker the wall thickness, the stiffer the spring becomes. Therefore, the spring 12' can exert a specific load against a rod, screw, or other object according to predetermined requirements. It is also possible to adjust the deflection range by altering the radius of curvature.

In FIG. 2, the spring 12 is contained within a cap member 36. The cap 36 includes a recess 38 that is preferably machined therein. The spring 12 sits in an uncompressed unloaded, state in the recess 38. The recess 38 includes an upper edge 40 and a lower edge 42 for respectively engaging the top 26 and bottom 28 of the lip 14.

The recess 38 includes side walls 37 (preferably annular) and a bottom wall or rigid plane 44. The spring 12 sits in the recess 38 with the lip 14 aligned with the rigid plane 44. The rigid plane 44 is simply the back of the machined recess 38 for the spring 12. When the spring 12 is compressed, the spring 12 presses against a portion of the rigid plane 44. The rigid plane 44 is aligned in relation to the lip 14, which in turn aligns with a groove 20 in the body 24 of the implant 46.

Another embodiment is shown in FIG. 3. In the embodiment, the lip 14 is angled in order to engage the implant body in such a way as to prevent spreading of the body 24 after seating the locking cap 36.

Figure 7:
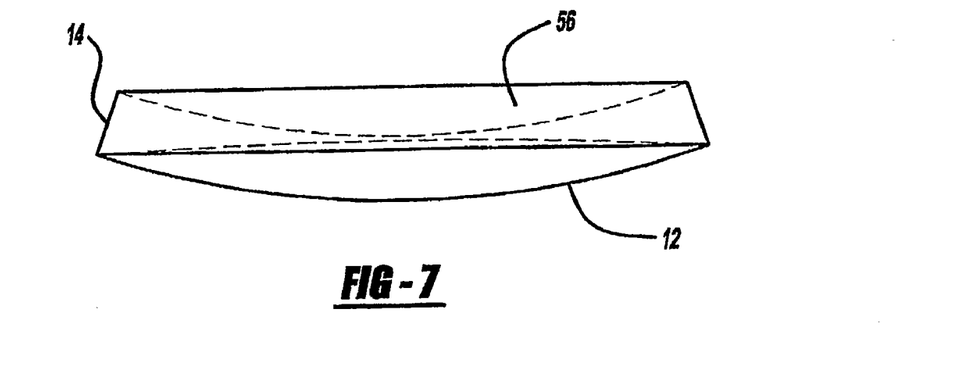
FIG. 7 is a side view of the an alternative embodiment of the locking mechanism of the present invention when positioned within a locking cap.

FIG. 7 shows another view of one embodiment of the locking cap 36 of the present invention. A cutout 48 is provided to allow clearance for a spring-rod interface in a body 24 using a rod 50. By allowing the rod 50 to be positioned within the locking cap 36, the overall height of the assembly is reduced. Since the radius of curvature 34 of the spring 12 can be altered as well the thickness and geometry of the spring, the cut-out 48 can be eliminated and still retain the same function.

Figure 8:
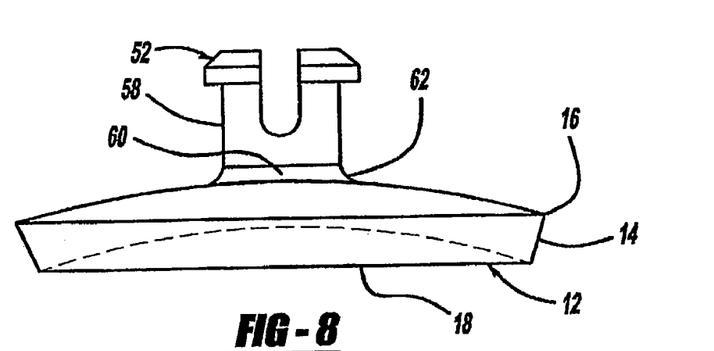
FIG. 8 is a side view of the locking mechanism of the present invention
Figure 9:
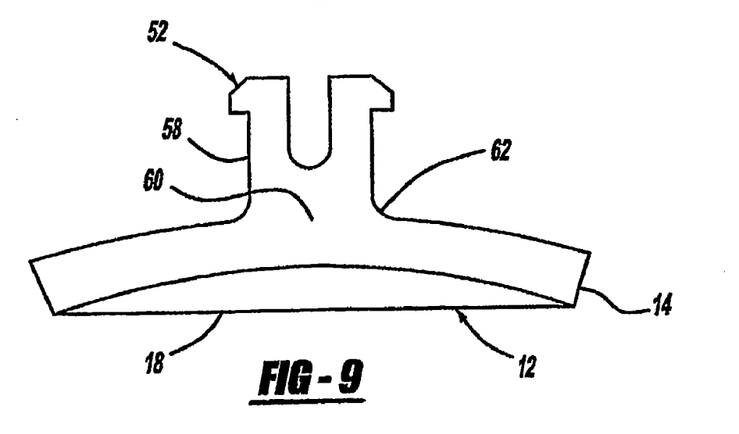
FIG. 9 is a side view of a concave shaped locking mechanism of the present invention.
Figure 10:
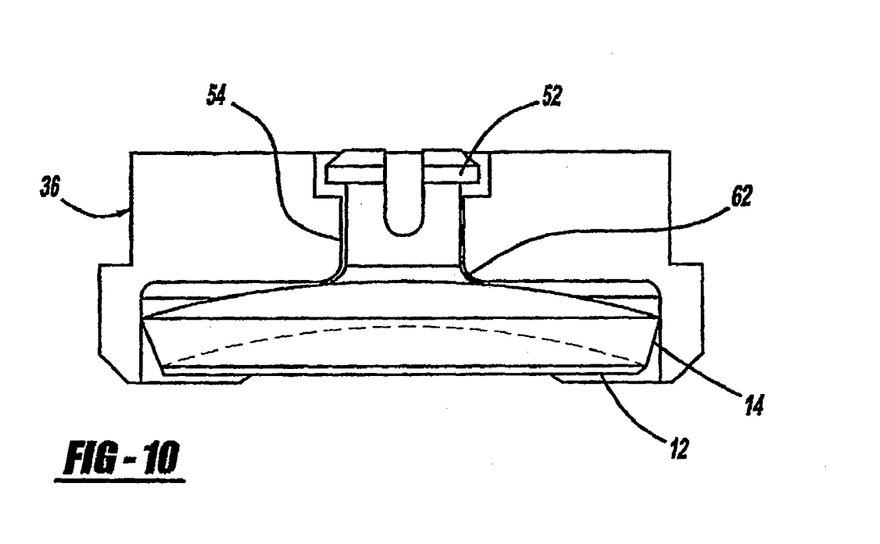
FIG. 10 is a cut view of the concave shaped locking mechanism of the present invention.
Figure 11:
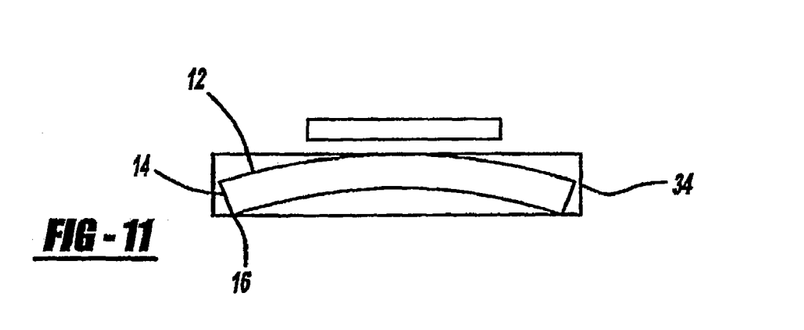
FIG. 11 is a side view of an inverted spring locking mechanism of the present invention.

Another embodiment involves inverting the spring 12" to allow more than one point of contact with the rod 50 or other component. As shown in FIG. 8, the spring 12" is inverted such that the central area 18 is now concave. This embodiment is held in place with the locking cap 36. There are multiple ways of maintaining the spring 12" in place. As shown in FIGS. 8 and 9, a stem 52 extends from the central portion 18 of the washer 12". The stem 52 can be snapped into a recess 54 in the locking cap 36, as shown in FIG. 10. Preferably, the stem 52 is slotted to allow flexure of a portion of the stem 52 so it will compress for engagement.

Figure 14:
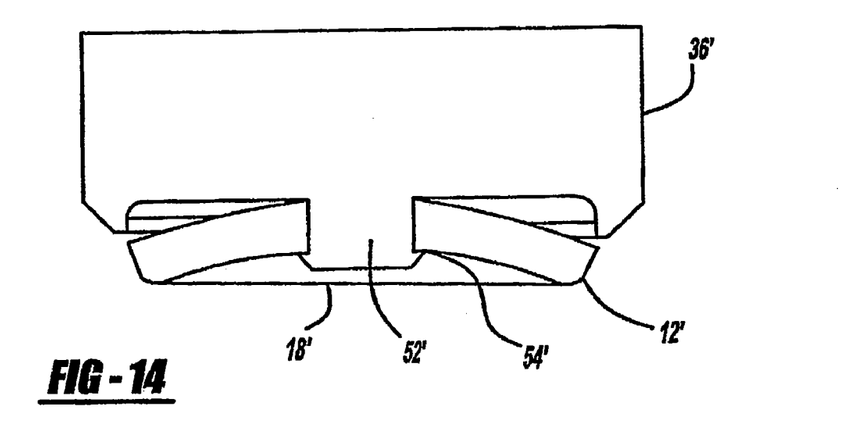
FIG. 14 is a side view of an alternative embodiment of the inverted spring locking mechanism of the present invention.
Figure 15:
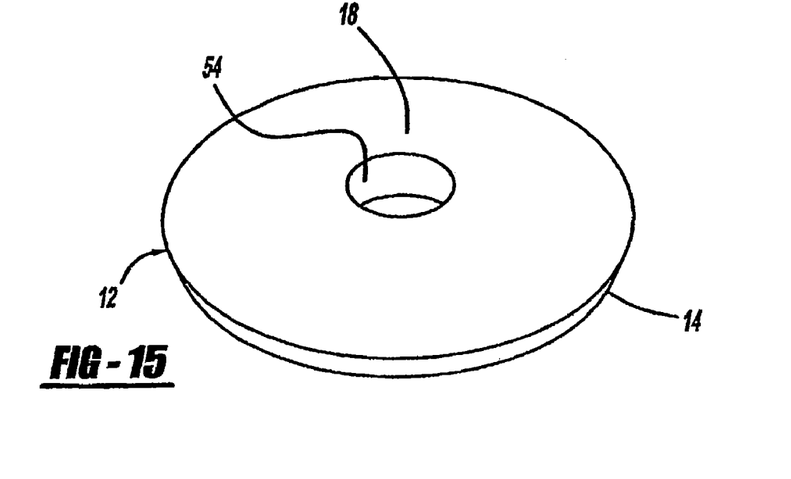
FIG. 15 is a top view of the locking mechanism, namely the spring, of the present invention.
Figure 16:
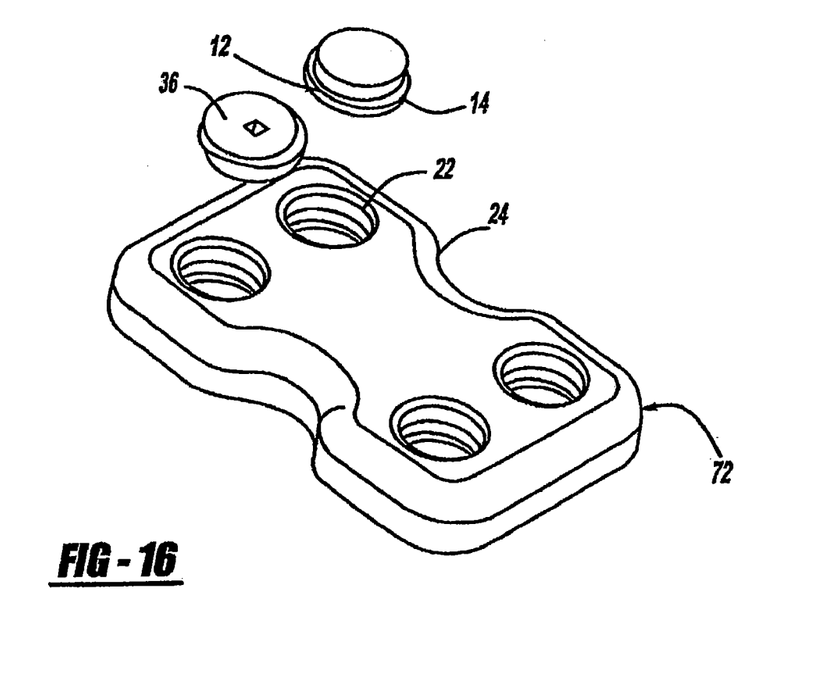
FIG. 16 is a view of a plate that can include either the threaded or non-threaded locking caps of the present invention.

Alternatively, the spring 12''' is inverted such that the central area 18' is now concave. This embodiment is held in place with the locking cap 36'. There are multiple ways of maintaining the spring 12''' in place. As shown in FIGS. 14, a stem 52' extends from the cap 36'. The stem 52' can be snapped into a recess 54' located at a central portion 18' in the washer 12''', as shown in FIG. 14. Preferably, the stem 52' is slotted to allow flexure of a portion of the stem 52' so it compresses for engagement.

The stem 52 can be eliminated and the spring 12 can snapped in an inverted condition into a recess 38 in the locking cap 36 as shown in FIGS. 2, 3 and 7. In such a case, as the central portion 18 of the spring 12'' is within the recess 38 a rod slot 56, as shown in FIG. 7, can be provided or an extension of the spring surface can be provided in order for the spring 12'' to engage the rod 50 or other implant surface. Such an embodiment is shown in FIG. 10.

The spring 12 can also have an extended portion 58 to engage the rod 50. When using a stem 52 for attaching the spring 12'' to the locking cap 36, the spring deflection 18 loses deflection uniformity across the spring. Since the stem 52 is relatively rigid, the spring 12'' at the attachment point 60 becomes more rigid. Deflection 34 occurs in the area between the outside edge 62 of the stem 52 and the radially peripheral edge 16 of the spring 12''. While this changes the stress in the spring 12'' due to its lack of uniformity, it also allows for adjusting the spring rate by adding thickness of material in a specific location. The adjustments lead to the ability to adjust spring rate by having a non-uniform wall thickness, such that the spring 12'' is thicker in the center 18 and thinner towards the edges 16.

Figure 12:
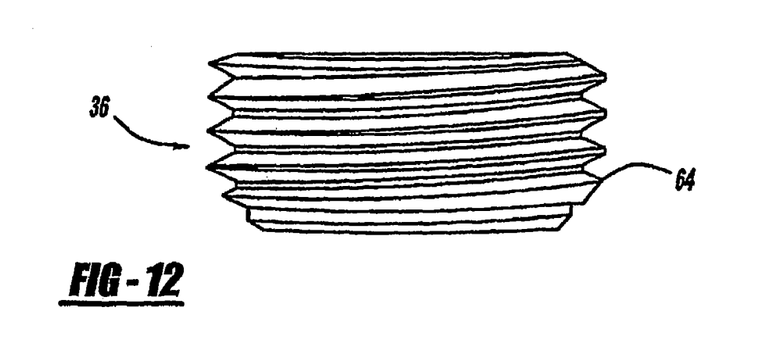
FIG. 12 is a side view of an alternative embodiment of the inverted spring locking mechanism of the present invention.
Figure 13:
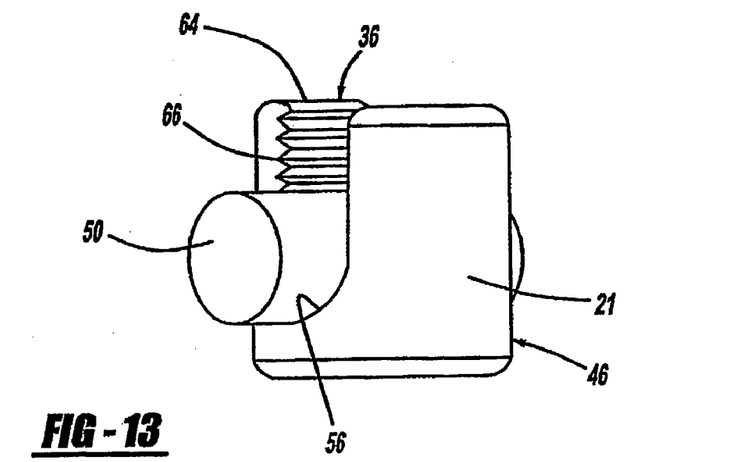
FIG. 13 is another view of the alternative embodiment of the inverted spring locking mechanism of the present invention.

While the cap 36 of the preferred embodiments does not use external threads 64, threads can be included, as shown in FIG. 12. The threads 64 can be used as a means to adapt the self-adjusting spring mechanism 12 described above. The locking cap 36 including threads 64 is shown in FIG. 13. The threads 64 provide controlled and calibrated locking of the implant 46 while eliminating a torque wrench. Another application is for use in a threaded hole 66 in which a screw rests. By tightening the locking cap 36, the spring 12 exerts force against the screw head, locking the screw to a plate 72. Such a configuration can be used in cervical and trauma plates. The threaded locking cap 36' can also be used in instruments as a substitution for a ball plunger.

In operation, the spring 12 is inserted a groove 20 into the body 24. Alternatively, the spring 12 can be inserted into a cap 36, which is then inserted into the body 24. FIG. 4 depicts how the locking mechanism 10 of the present invention is inserted. FIG. 4 depicts the embodiment including a locking cap 36. The locking cap 36 is engaged with an interior wall 22 of arms 68 of an implant body 24. Once the cap 36 is positioned such that the lip 14 of the locking mechanism 10 is entrained within the groove 20 on the interior wall 22 of the body 24, the cap 36 is fixedly seated in the groove 20 in the body 24.

The arms 68 of the body 24 are formed by cuffing a U-shaped channel 70 that allows a rod 50 to seat in a rod seat 56. The configuration of the arms 68 and the material that forms the arms 68 enable the arms 68 to be flexible. The flexibility is controlled by the wall thickness, curvature, and geometry. Moving the rod seat 566 or making it larger can affect one or both arms 68 of the body 24. By allowing enough flexibility, the locking cap 36 can be used to push the arms 68 open enough to allow the locking cap 36 to seat in the groove 20 in the body 24. Once the locking cap 36 reaches the right location, the lip 14 engages the body groove 20, allowing the body 24 to spring back to a resting condition.

Figure 5:
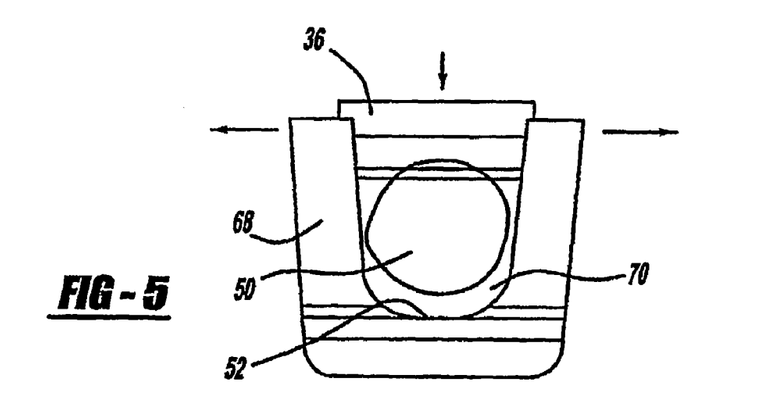
FIG. 5 is a side view showing the spreading of the implant body upon insertion of the locking mechanism.
Figure 6:
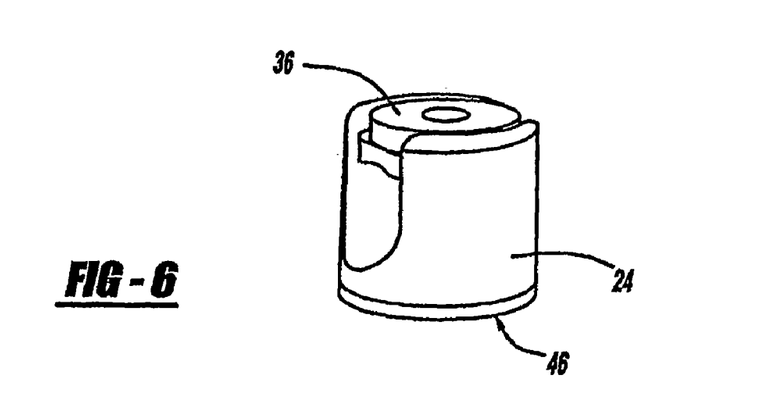
FIG. 6 is a side view showing that the implant body returns to an initial condition once the locking mechanism is fully seated.

FIG. 5 shows that pushing the locking cap 36 into the body 24 causes the arms 68 to spread. Once the locking cap 36 is fully seated, the arms 68 return to the initial condition. The final configuration is shown in FIG. 6.

Throughout this application, author, year, and patents by number reference various publications, including United States patents. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology that has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A spinal fixation assembly comprising:
a fixing mechanism defining a seat for receiving a spinal fixation rod; and
a locking mechanism comprising a locking means adapted to be moved axially along a plane perpendicular to the seat until the locking mechanism is non-threadably fixed in position relative to the fixing mechanism while being self-adjusting relative thereto for locking a rod in place within the fixing mechanism.

2. The spinal fixation assembly according to claim 1, wherein said locking means is deformable.

3. The spinal fixation assembly according to claim 2, wherein said deformable locking means is a spring.

4. The spinal fixation assembly according to claim 3, wherein said spring is selected from the group consisting essentially of a washer, a flexible disc, and other flexible devices.

5. The spinal fixation assembly according to claim 4, wherein a bottom surface of said spring is concave.

6. The spinal fixation assembly according to claim 4, wherein a bottom surface of said spring is convex.

7. The spinal fixation assembly according to claim 1, wherein said locking means further includes spring retaining means for retaining said locking means in the assembly.

8. The spinal fixation assembly according to claim 7, wherein said spring retaining means is a groove in the assembly.

9. The spinal fixation assembly according to claim 7, wherein said spring retaining means is a cap insertable into the assembly.

10. The spinal fixation assembly according to claim 8, wherein said cap includes a threaded outer surface.

11. The spinal fixation assembly according to claim 9, further including fixing means on an upper surface of said locking means for fixing said locking means within a groove in the locking cap.

12. The spinal fixation assembly according to claim 9, further including fixing means on a bottom surface of said the locking cap for fixing said locking means within a groove in the locking cap and a recess for matingly engaging said fixing means.

13. The spinal fixation assembly according to claim 11, wherein said fixing means is a stem.

14. The spinal fixation assembly according to claim 13, wherein said stem is a rigid rod centrally affixed to the upper surface of said locking means.

15. The spinal fixation assembly according to claim 14, wherein said stem includes a central slot on an upper surface opposite an end affixing said stem to said locking means.

16. A spinal fixation assembly comprising:
- an implant body defining a seat for receiving a spinal fixation rod, the implant body further defining a circumferential groove; and
- a locking mechanism including a spring biased portion and an edge portion, the edge portion snap-fittingly engages the groove such that the locking mechanism is retained relative to the implant body with the spring biased portion facing the seat.

17. The spinal fixation assembly according to claim 16 wherein the locking mechanism is a spring including the edge portion and the spring biased portion.

18. The spinal fixation assembly according to claim 16 wherein the locking mechanism includes a cap including the edge portion and a spring retained within the cap and defining the spring biased portion.

* * * * *